(12) United States Patent
Castleman et al.

(10) Patent No.: US 7,981,157 B2
(45) Date of Patent: Jul. 19, 2011

(54) SELF-CONTAINED EXPANDABLE IMPLANT AND METHOD

(75) Inventors: David W. Castleman, Germantown, TN (US); Eric S. Heinz, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1068 days.

(21) Appl. No.: 11/412,507

(22) Filed: Apr. 27, 2006

(65) Prior Publication Data

US 2007/0255407 A1  Nov. 1, 2007

(51) Int. Cl.
*A61F 2/44* (2006.01)
(52) U.S. Cl. .................................... 623/17.15
(58) Field of Classification Search .............. 606/248, 606/249, 54, 57, 58, 62, 63; 623/17.11–17.16
See application file for complete search history.

(56) References Cited

U.S. PATENT DOCUMENTS

| | | |
|---|---|---|
| 2,333,033 A | 10/1943 | Mraz |
| 3,701,605 A | 10/1972 | Morishima |
| 4,157,715 A | 6/1979 | Westerhoff |
| 4,289,123 A | 9/1981 | Dunn |
| 4,386,603 A | 6/1983 | Mayfield |
| 4,401,112 A | 8/1983 | Rezaian |
| 4,553,273 A | 11/1985 | Wu |
| 4,554,914 A | 11/1985 | Kapp et al. |
| 4,599,086 A | 7/1986 | Doty |
| 4,636,217 A | 1/1987 | Ogilvie et al. |
| 4,657,550 A * | 4/1987 | Daher .................. 623/17.11 |
| 4,892,546 A | 1/1990 | Kotz et al. |
| 5,002,576 A | 3/1991 | Fuhrmann et al. |
| 5,236,460 A | 8/1993 | Barber |
| 5,281,226 A | 1/1994 | Davydov et al. |
| 5,290,312 A | 3/1994 | Kojimoto et al. |
| 5,336,223 A | 8/1994 | Rogers |
| 5,405,391 A | 4/1995 | Hednerson et al. |
| 5,413,602 A | 5/1995 | Metz-Stavenhagen |
| 5,458,641 A | 10/1995 | Ramirez Jimenez |
| 5,480,442 A | 1/1996 | Bertagnoli |
| 5,571,192 A | 11/1996 | Schonhoffer |
| 5,658,335 A | 8/1997 | Allen |
| 5,702,453 A | 12/1997 | Rabbe et al. |
| 5,702,455 A | 12/1997 | Saggar |
| 5,723,013 A | 3/1998 | Jeanson et al. |
| 5,776,197 A | 7/1998 | Rabbe et al. |
| 5,776,198 A | 7/1998 | Rabbe et al. |
| 5,800,547 A | 9/1998 | Schafer et al. |
| 5,916,267 A | 6/1999 | Tienboon |
| 5,989,290 A | 11/1999 | Biedermann et al. |

(Continued)

FOREIGN PATENT DOCUMENTS

DE  3023942  1/1982

(Continued)

OTHER PUBLICATIONS

European Patent Office, International Search Report and Written Opinion of PCT/US2007/065845, Sep. 25, 2007, 13 pages.

*Primary Examiner* — Eduardo C Robert
*Assistant Examiner* — Elana B Fisher (57) ABSTRACT

Embodiments of the invention include expandable, implantable devices and methods having internally contained expansion mechanisms. Devices expand linearly to provide secure fixation between or among anatomical structures. In some embodiments, an implant replaces one or more vertebral bodies of the spine.

25 Claims, 5 Drawing Sheets

U.S. PATENT DOCUMENTS

| | | | |
|---|---|---|---|
| 6,015,436 A | 1/2000 | Schonhoffer | |
| 6,045,579 A | 4/2000 | Hochshuler et al. | |
| 6,080,193 A | 6/2000 | Hochshuler et al. | |
| 6,126,660 A | 10/2000 | Dietz | |
| 6,176,881 B1 | 1/2001 | Schar et al. | |
| 6,190,413 B1 | 2/2001 | Sutcliffe | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,296,665 B1* | 10/2001 | Strnad et al. | 623/17.16 |
| 6,299,644 B1 | 10/2001 | Vanderschot | |
| 6,344,057 B1 | 2/2002 | Rabbe et al. | |
| 6,352,556 B1 | 3/2002 | Kretschmer et al. | |
| 6,375,683 B1 | 4/2002 | Crozet et al. | |
| 6,395,034 B1 | 5/2002 | Suddaby | |
| 6,454,806 B1 | 9/2002 | Cohen et al. | |
| 6,524,341 B2 | 2/2003 | Lang et al. | |
| 6,562,074 B2 | 5/2003 | Gerbec et al. | |
| 6,616,695 B1 | 9/2003 | Crozet et al. | |
| 6,648,917 B2 | 11/2003 | Gerbec et al. | |
| 6,660,038 B2 | 12/2003 | Boyer, II et al. | |
| 6,719,796 B2 | 4/2004 | Cohen et al. | |
| 6,752,832 B2 | 6/2004 | Neumann | |
| 6,783,547 B2 | 8/2004 | Castro | |
| 6,866,682 B1 | 3/2005 | An et al. | |
| 6,908,485 B2 | 6/2005 | Crozet et al. | |
| 2002/0072801 A1 | 6/2002 | Michelson | |
| 2002/0082695 A1* | 6/2002 | Neumann | 623/17.11 |
| 2002/0161441 A1 | 10/2002 | Lang et al. | |
| 2003/0045877 A1 | 3/2003 | Yeh | |
| 2004/0049271 A1 | 3/2004 | Biedermann et al. | |
| 2004/0059271 A1* | 3/2004 | Berry | 602/32 |
| 2004/0153160 A1 | 8/2004 | Carrasco | |
| 2004/0162618 A1 | 8/2004 | Mujwid et al. | |
| 2004/0172129 A1* | 9/2004 | Schafer et al. | 623/17.11 |
| 2004/0181283 A1 | 9/2004 | Boyer, II et al. | |
| 2004/0186569 A1* | 9/2004 | Berry | 623/17.11 |
| 2005/0060036 A1 | 3/2005 | Schultz et al. | |
| 2005/0090898 A1 | 4/2005 | Berry et al. | |
| 2005/0113921 A1 | 5/2005 | An et al. | |
| 2005/0234550 A1 | 10/2005 | Metz-Stavenhagen | |
| 2006/0058879 A1 | 3/2006 | Metz-Stavenhagen | |
| 2006/0241621 A1* | 10/2006 | Moskowitz et al. | 606/72 |
| 2006/0241770 A1* | 10/2006 | Rhoda et al. | 623/17.15 |

FOREIGN PATENT DOCUMENTS

| | | |
|---|---|---|
| DE | 3729600 | 3/1989 |
| DE | 4012622 | 7/1991 |
| DE | 9107494 | 10/1991 |
| DE | 4109941 | 10/1992 |
| DE | 4409392 | 9/1995 |
| DE | 4423257 | 1/1996 |
| DE | 19500170 | 2/1996 |
| DE | 19509317 | 9/1996 |
| DE | 19519101 | 11/1996 |
| DE | 19622827 | 12/1997 |
| DE | 29616778 | 3/1998 |
| DE | 19804765 | 8/1999 |
| DE | 20207853 | 5/2002 |
| DE | 20213013 | 1/2003 |
| DE | 10357926 | 9/2005 |
| DE | 20320974 | 2/2007 |
| EP | 0188954 | 7/1986 |
| EP | 0290767 | 11/1988 |
| EP | 0490159 | 6/1992 |
| EP | 0567424 | 10/1993 |
| EP | 0832622 | 4/1998 |
| EP | 0968692 | 1/2000 |
| EP | 1080703 | 3/2001 |
| EP | 1188424 | 3/2002 |
| EP | 1219266 | 7/2002 |
| FR | 2774280 | 1/1998 |
| JP | 62164458 | 7/1997 |
| SU | 1560184 | 4/1990 |
| SU | 1739989 | 6/1992 |
| WO | 9201428 | 2/1992 |
| WO | 9418913 | 9/1994 |
| WO | 9525486 | 9/1995 |
| WO | 9617564 | 6/1996 |
| WO | 9637170 | 11/1996 |
| WO | 9747258 | 12/1997 |
| WO | 9846173 | 10/1998 |
| WO | 9939665 | 8/1999 |
| WO | 9956675 | 11/1999 |
| WO | 9963913 | 12/1999 |
| WO | 0023013 | 4/2000 |
| WO | 0197744 | 6/2001 |
| WO | 03096937 | 11/2003 |
| WO | 2004096103 | 11/2004 |
| WO | 2004100837 | 11/2004 |
| WO | 2005055887 | 6/2005 |

* cited by examiner

SELF-CONTAINED EXPANDABLE IMPLANT AND METHOD

FIELD OF THE INVENTION

The present invention relates generally to the field of replacing portions of the human structural anatomy with medical implants, and more particularly relates to an expandable implant and method for replacing skeletal structures such as one or more vertebrae or long bones.

BACKGROUND

Figures 1, 2:
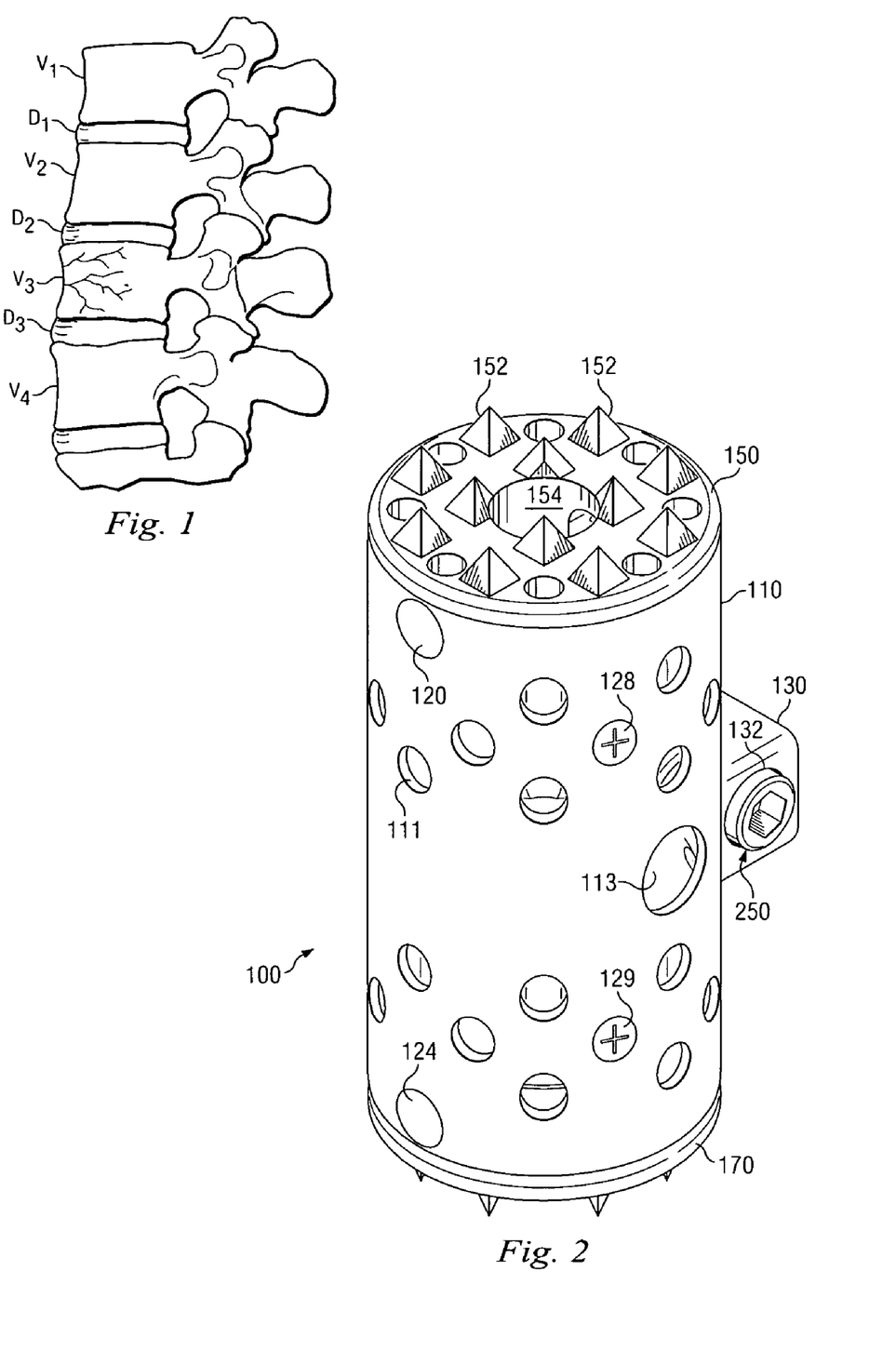
FIG. 1 is an elevation view of a segment of a lumbar spine.
FIG. 2 is a perspective view of an expandable implant embodiment.

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Excision of at least the generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. Most commonly, the implant inserted between the vertebrae is designed to facilitate fusion between remaining vertebrae. Sometimes the implant is designed to replace the function of the excised vertebra and discs. All or part of more than one vertebrae may be damaged and require removal and replacement in some circumstances.

Many implants are known in the art for use in a corpectomy procedure. One class of implants is sized to directly replace the vertebra or vertebrae that are being replaced. Another class of implants is inserted into the body in a collapsed state and then expanded once properly positioned. Expandable implants may be advantageous because they allow for a smaller incision when properly positioning an implant. Additionally, expandable implants may assist with restoring proper loading to the anatomy and achieving more secure fixation of the implant. Implants that include insertion and expansion mechanisms that are narrowly configured may also provide clinical advantages. In some circumstances, it is desirable to have vertebral endplate contacting surfaces that effectively spread loading across the vertebral endplates. Effective implants should also include a mechanism for maintaining the desired positions, and in some situations, being capable of collapsing. Fusion implants with an opening may also be advantageous because they allow for vascularization and bone growth through all or a portion of the implant.

Expandable implants may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

SUMMARY

One embodiment of the invention is an expandable medical implant for supporting skeletal structures including a body and a sprocket disposed within the body having gears configured to receive a turning mechanism to rotate the sprocket, the sprocket including a first end with a threaded portion and a second end with a threaded portion. The embodiment may also include a first end component sized to engage with the threaded portion of the sprocket first end and a second end component sized to engage with the threaded portion of the sprocket second end.

A further embodiment of the invention is an expandable medical implant for supporting skeletal structures including a body and an expansion means disposed within the body for converting rotational movement substantially transverse to the longitudinal axis into linear expansion of the implant along the axis. The embodiment may also include a first end component sized to engage with the expansion means and be moved away from the body by operation of the expansion means and a second end component sized to engage with the expansion means and be moved away from the body by operation of the expansion means. The expansion means is captured within the body for protection of tissue adjacent to the skeletal structures.

Another embodiment of the invention is a method of placing an expandable medical implant within a spinal column. The method embodiment may include making an incision adjacent to a vertebral body and removing at least a portion of the vertebral body. Included in the embodiment are the expandable medical implant with a body, an expansion means disposed within the body for converting rotational movement into linear expansion of the implant, a first end component sized to engage with the expansion means and be moved away from the body by operation of the expansion means, and a second end component sized to engage with the expansion means and be moved away from the body by operation of the expansion means; and a surgical instrument comprising a cannula and an inner shaft disposed at least in part within the cannula, the inner shaft configured to couple with the expansion means. The method may also include releasably attaching the cannula to the body, inserting the expandable medical implant at least in part into a volume left open after removal of the portion of the vertebral body, rotating the inner shaft to activate the expansion means, detaching the cannula from the body, and removing the surgical instrument through the incision.

Further aspects, forms, embodiments, objects, features, benefits, and advantages of the present invention shall become apparent from the detailed drawings and descriptions provided herein.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 3:
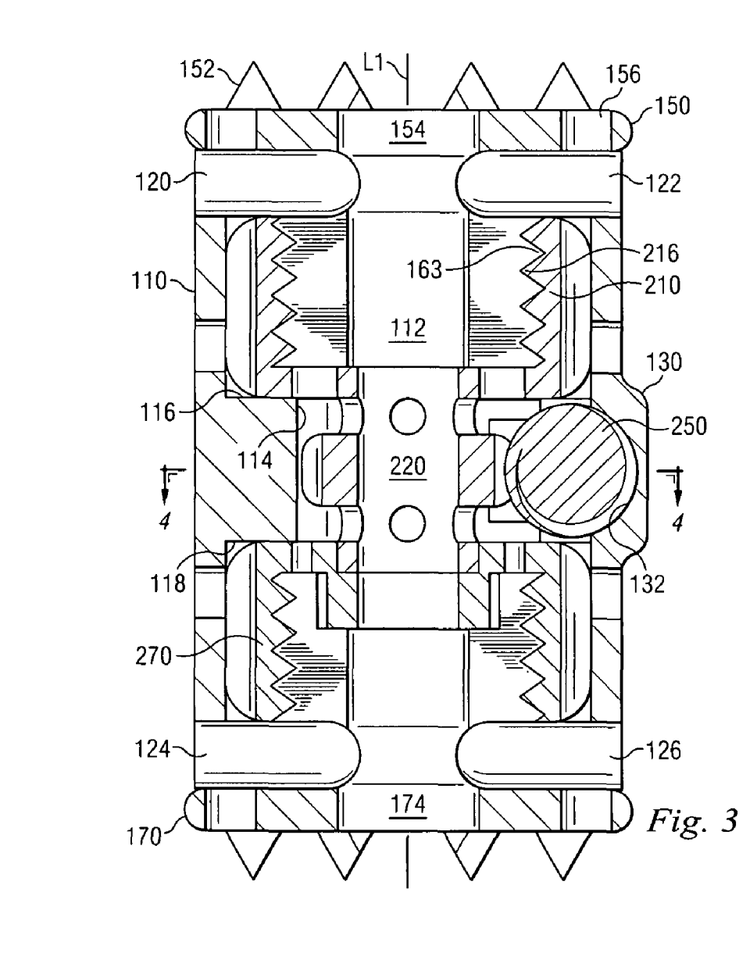
FIG. 3 is a side cross-sectional view of the implant of FIG. 2.

Referring now to FIG. 2, there is shown an expandable implant 100 according to one aspect of the present invention. Expandable implant 100 is sized and shaped for insertion into the space remaining in the vertebral column after removal of vertebra $V_3$ and discs $D_2$ and $D_3$ in FIG. 1. Expandable implant 100 includes an outer housing 110 having a number of openings 111 extending from the outer surface to an interior cavity 112. In the illustrated embodiment best seen in FIG. 3, housing 110 is a substantially cylindrical tube having a relatively thin wall thickness in comparison to its diameter. The housing 110 extends along a longitudinal axis $L_1$ (FIG. 3). Housing 110 defines an external protrusion 130 having a cylindrical aperture 132 oriented transverse to and spaced laterally from longitudinal axis $L_1$. The protrusion 130 has a proximal opening 132 and an opposite distal opening spaced along axis $L_2$.

Figure 6:
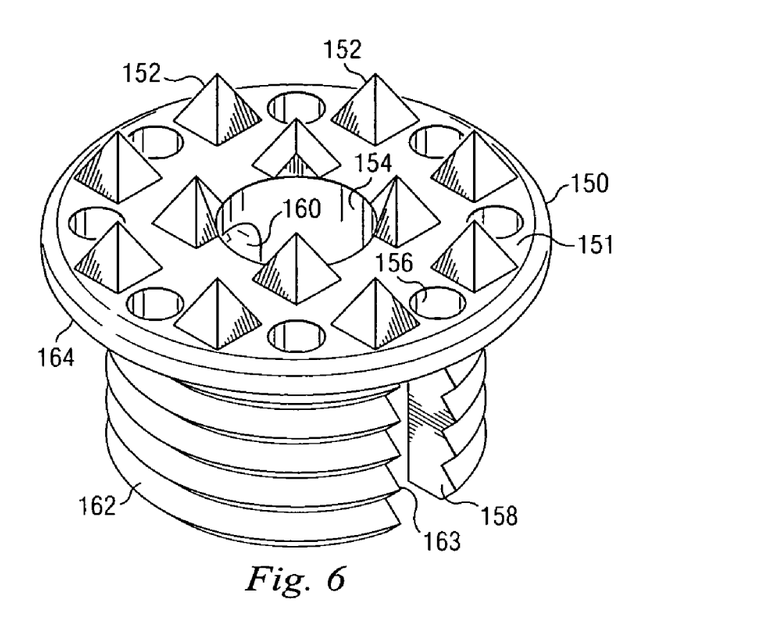
FIG. 6 is a perspective view of an end component of the implant of FIG. 2.

Referring now to FIGS. 1-3, and 4, additional elements of the illustrated embodiment will be further described. Expandable implant 100 includes an upper bone engaging component 150 and a lower bone engaging component 170. Bone engaging component 150 includes a series of projections 152 extending from the substantially planar surface 151. The projections 152 are adapted and configured for engagement and penetration of adjacent bone structures. Bone engaging component 150 further includes a central aperture 154 and a plurality of minor apertures 156. It will be understood that the central aperture and the minor apertures allow for the communication of bone growth promoting substances and bodily fluids to encourage and enhance bone ingrowth into expandable device 100. As shown in FIG. 6, bone engaging component 150 further includes a pair of opposing channels 158 and 160 extending away from upper surface 151 and being open at the opposite end. The upper portion of the bone engaging component 150 includes an annular flange 164 defining a rim and projecting cylindrical body 162 having an external thread 163 defined on the outer surface. In one aspect, the threads 163 are a right-handed thread form. The threads 163 and cylindrical body 162 are interrupted by channels 158 and 160. The lower bone engaging component 170 has substantially identical features in the inverse orientation to the upper bone engaging component 150 and will not be further described herein.

Figure 5:
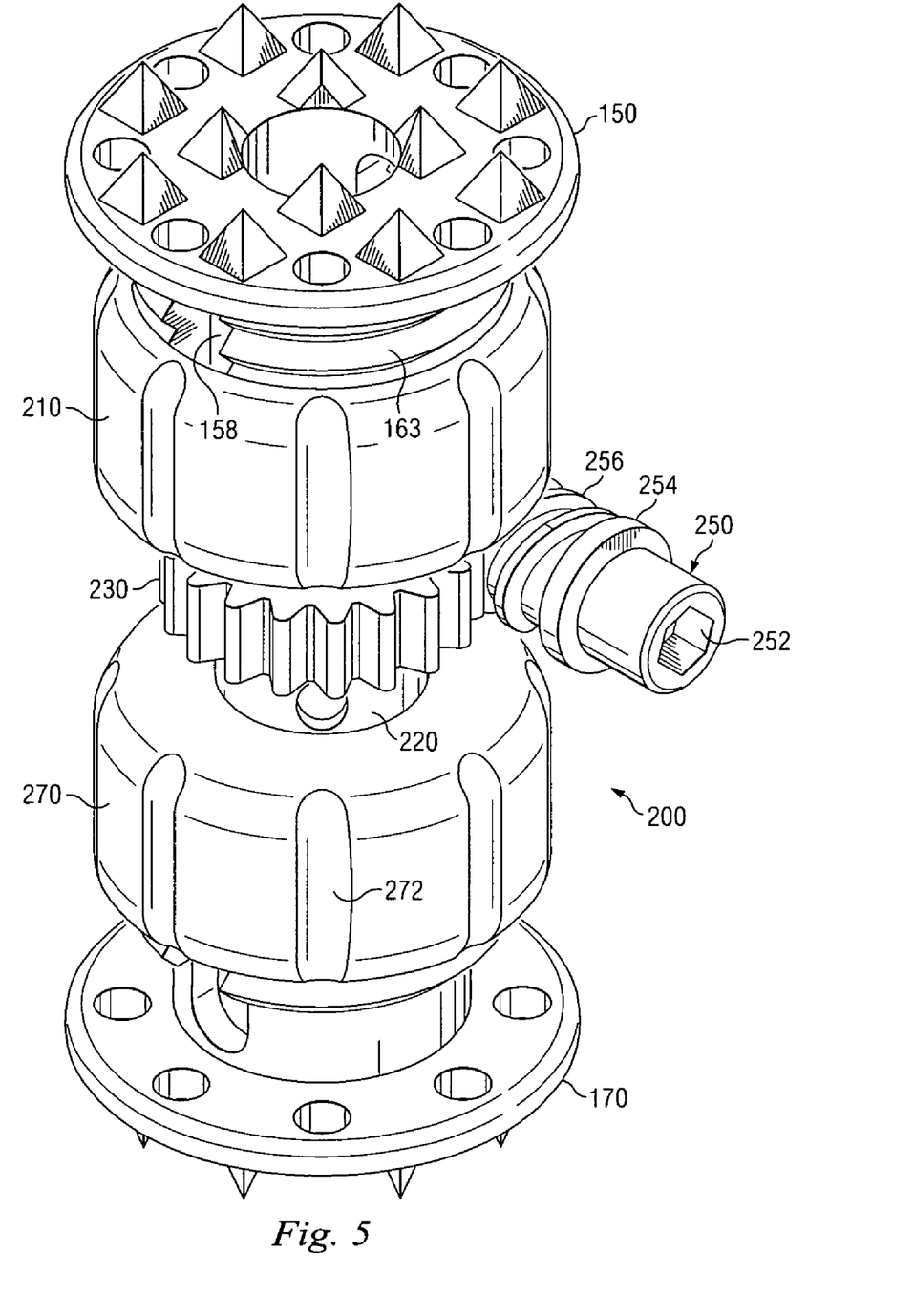
FIG. 5 is a partial cut-away view of the implant of FIG. 2.
Figure 7:
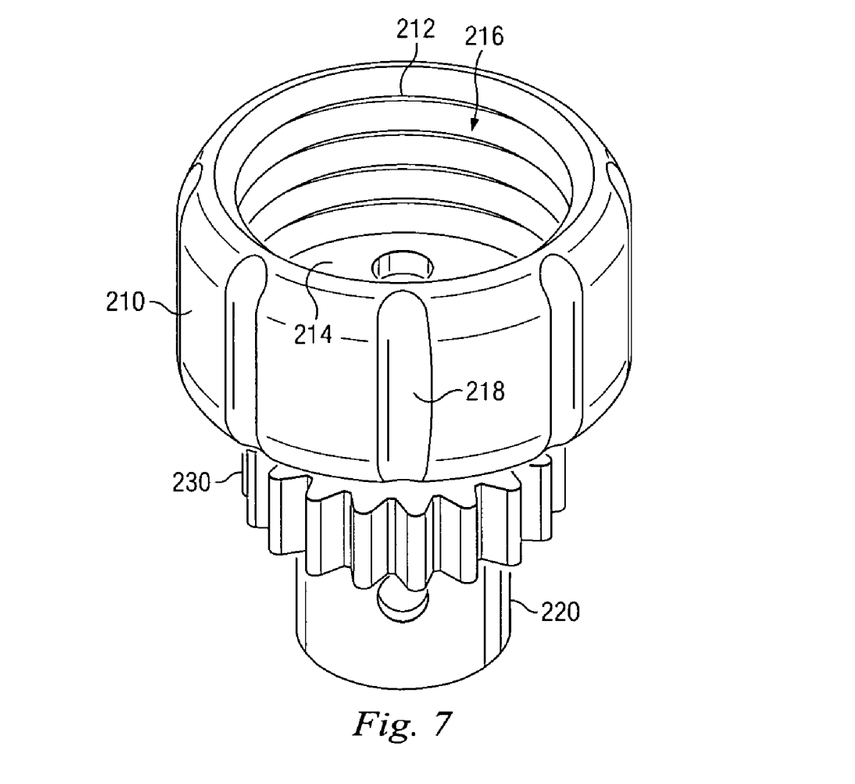
FIG. 7 is a perspective view of a sprocket of the implant of FIG. 2.

Referring now to FIG. 5, there is shown an expansion assembly 200 in accordance with one aspect of the present invention. Expansion assembly 200 includes an upper sprocket assembly 210 and a lower sprocket assembly 270. As shown in greater detail in FIG. 7, upper sprocket assembly 210 includes a central chamber 216 defined by an annular wall having internal threads 212 extending around the inner surface. In the illustrated embodiment, the inner surface is cylindrical and the threads are right-handed threads. Chamber 216 is further defined by a floor 214 having a plurality of holes extending there through to allow communication of bodily fluids and bone growth. The exterior of the upper sprocket assembly includes a plurality of longitudinally extending grooves 218. A central drive shaft 220 is integrally formed in this embodiment with upper sprocket assembly 210. A multi-toothed sprocket gear 230 is disposed on drive shaft 220. Multi-toothed gear 230 has a plurality of longitudinally extending gear teeth oriented along the longitudinal axis $L_1$ of the device and having a center of rotation in substantial alignment with longitudinal axis $L_1$.

Referring now to FIG. 5, there is shown a lower sprocket assembly 270 having features substantially identical to the upper portion of upper sprocket assembly 210. More specifically, as shown in FIG. 3, lower sprocket assembly 270 includes an internally left-hand threaded chamber open towards the lower portion of the device and a plurality of longitudinally extending external grooves 272 on the exterior of the device. In the illustrated embodiment, lower end of driveshaft 220 is received within a similarly sized bore on lower sprocket assembly 270. In the illustrated embodiment, there is a tight interference fit between the driveshaft 220 and the bore of lower sprocket assembly 270. In this manner, the upper sprocket assembly 210 is press fit to the lower sprocket assembly 270 such that they maintain their rotational relationship as gear 230 is rotated. In an alternative embodiment, the bore in lower sprocket assembly 270 includes at least one a channel or passageway and a distal end of driveshaft 220 includes at least one key or projection configured to be received within the passageway. In this manner, a greater amount of rotational force or torque may be transmitted between driveshaft 220 and lower sprocket assembly 270 without slippage there between. Although an interference fit or keyed engagement has been described and illustrated, it is contemplated that other forms may be utilized to interconnect the upper and lower sprocket assemblies. For example, in other embodiments the connection is maintained by adhesive pins, threading, and/or formation as an integral component.

Figure 4:
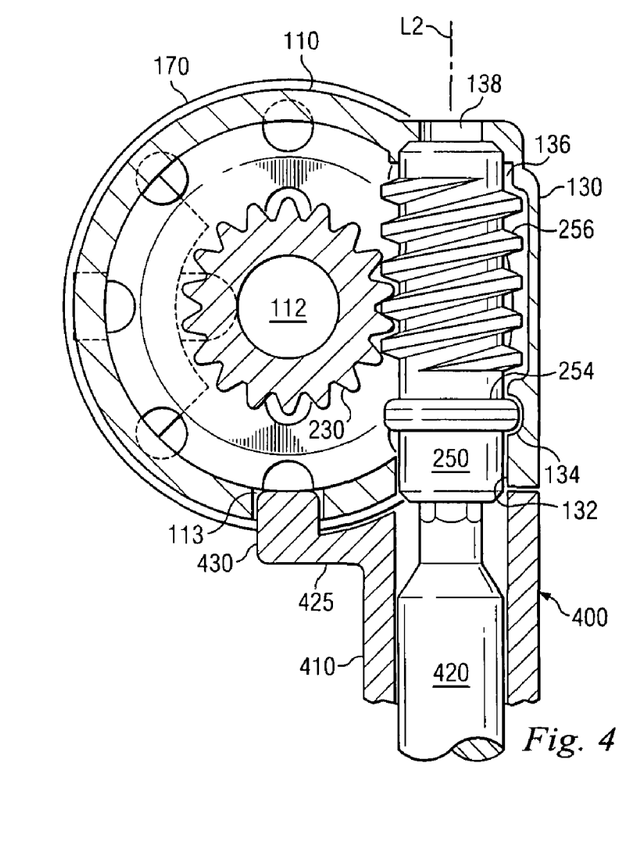
FIG. 4 is a partial longitudinal cross-sectional view of the implant of FIG. 3.
Figure 8:
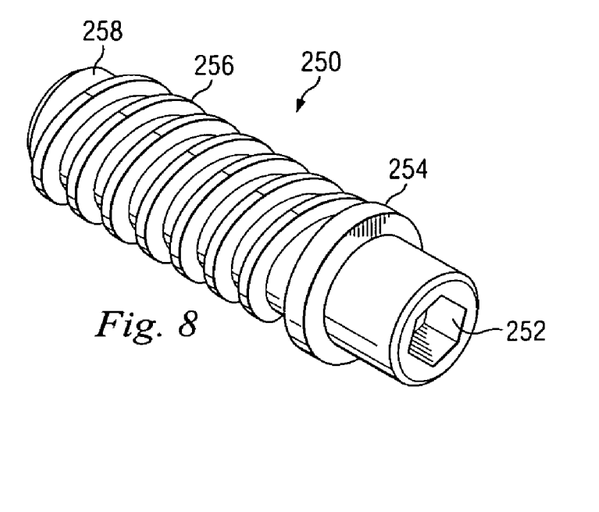
FIG. 8 is a perspective view of a worm gear or the implant of FIG. 2.

Associated with the expansion assembly 200 is a worm gear 250. Worm gear 250 is best seen in FIGS. 4 and 8. Worm gear 250 includes a drive socket 252 on its proximal end and a bearing shoulder 254 adjacent drive socket 252. A helical gear 256 extends between shoulder 254 and distal end 258. In one aspect of the present embodiment, a further drive pattern (not shown) is formed adjacent distal end 258.

The expansion assembly 200 is assembled as shown in FIG. 5. Within the interior cavity 112, housing 110 includes an inner annular flange 114 defining an upper bearing surface configured to engage at least a portion of upper sprocket assembly 210 and a lower bearing surface 118 configured to engage at least a portion of lower sprocket 270. The interior 112 of housing 110 includes an open area adjacent projecting flange 114 such that gear 230 may spin freely without obstruction. Thus, sprocket 230 is completely within the perimeter of the housing 110. The upper socket assembly 210 is positioned into the upper portion of the interior cavity 112. In a similar manner, the lower sprocket assembly 270 is positioned in the lower portion of cavity 112. The lower portion of drive shaft 220 is press fit into engagement with lower sprocket assembly 270 to form a unitary sprocket assembly completely within the outer perimeter of the housing 110.

Worm gear 250 is positioned within aperture 132 as shown in FIGS. 3 and 4. An annular groove 134 is defined in aperture 132 and is adapted to receive bearing shoulder 254 of worm gear 250. The helical threads 256 are positioned within cylindrical chamber 136 and the distal end 258 is positioned adjacent distal opening 138. The worm gear 250 extends along drive axis $L_2$ as shown in FIG. 4. It will be appreciated that in the illustrated embodiment, drive axis $L_2$ is substantially perpendicular to extension axis $L_1$. Moreover, extension axis $L_1$ extending in a centered manner through internal chamber 112 is laterally offset from drive axis $L_2$ by ½ the diameter of helical gear 256 and ½ the diameter of sprocket gear 230. In this manner, helical gear 256 may engage and mesh with longitudinally extending gear teeth of sprocket gear 230. As a result of this engagement, rotational movement applied to internal drive socket 252 tending to rotate helical gears 256 along axis $L_2$ is translated into rotational movement about expansion axis $L_1$.

Upper bone engaging component 150 is threadedly received within internally threaded aperture 216 and threadedly engages internal threads 212. In a similar manner, lower bone engaging component 170 is threaded into the internally threaded aperture of lower sprocket 270. The upper bone engaging component 150 is threadedly received within the upper sprocket assembly 210 until it has been substantially advanced to its final position. Channel 158 and channel 160 are aligned with openings through housing 110 and then pins 120 and 122 are passed through apertures formed in housing 110 and into channels 158 and 160, respectively. In this manner, bone engaging component 150 is locked in rotational alignment with housing 110 but passages 158 and 160 allow longitudinal movement of bone engaging component 150 along the longitudinal axis $L_1$. In a similar manner, lower bone engaging component 170 has a pair of opposing channels formed in its threaded cylindrical portion. When assembled in the position shown in FIG. 3, a pair of pins 124 and 126 is positioned within the channels to retain the lower bone engaging component 170 in a rotationally locked engagement with respect to housing 110 while allowing longitudinal movement of the lower bone engaging component 170 in response to threaded engagement with lower sprocket 270.

In use, a healthcare provider obtains surgical access to a segment of the vertebral column. A damaged vertebral body such as $V_3$ is at least partially removed along with the adjacent soft tissue structure such as $D_2$ and $D_3$. An expandable device 100 is inserted into the remaining space in the substantially collapsed condition shown in FIG. 2. As shown in FIG. 4, an insertion tool 400 is engaged to the device. Insertion tool 400 includes a cannula 410 and an internal drive shaft 420 terminating in a hex drive for mating with socket 252. A locking arm 425 extends medially and includes a locking pin 430. The device 100 is oriented such that driving tool 400 having an external hex drive shaft is engaged with driving socket 252 of worm gear 250. Additionally, in a preferred aspect the insertion tool 400 engagement projection 430 extends into enlarged aperture 113. In this manner, as rotational force is applied to internal drive socket 252 the insertion member can maintain the relative position of expansion implant 100. Rotation of worm gear 250 along drive axis $L_2$ is translated through the engagement with sprocket gear 230 into rotational movement along expansion axis $L_1$. Rotation of sprocket gear 230 results in corresponding rotation of upper sprocket assembly 210 and lower sprocket assembly 270.

As a result of the threaded engagement between the sprocket assemblies 210 and 270 with the upper bone engaging component 150 and the lower bone engagement component 170, respectfully, rotation of the sprocket assembly about longitudinal axis $L_1$ causes advancement of both the upper and lower bone engagement assemblies along the longitudinal axis $L_1$. It will be appreciated that continued expansion along the longitudinal axis will bring projections 152 of the upper surface and corresponding projections of the lower bone engagement component into contact with the corresponding upper and lower bone surfaces. Further rotation applied to the worm gear will be translated into rotational movement of the sprocket assembly about longitudinal axis $L_1$ and will tend to lengthen the device and drive the projections into the bone. It will be appreciated that the projections may in one aspect, be driven into the bone until the surface 151 engages the upper bone surface.

Alternatively in another embodiment, the bone engaging projections do not extend completely into the bone. In this implantation, it is contemplated that at least some subsidence of the bone over time will occur and the upper bone surface will receive a greater extent of the projections until the bone comes to rest on the surface 151. While projections 152 have been illustrated as pyramid shaped spikes, in alternative embodiments the projections take the form of cones, blades, keels, fins, ridges, pegs or any other surface projection. Further, the surface 151 may be formed such that recesses in the surface create projections in a bone ingrowth type surface allowing bone to grow into the surface or to interdigitate with native bone on the endplates.

Should the device need to be repositioned or revised, rotation of the worm gear in the opposite direction will have a tendency to collapse the expandable device such that it can be extracted from the patient or repositioned into a more desirable location.

Figure 9:
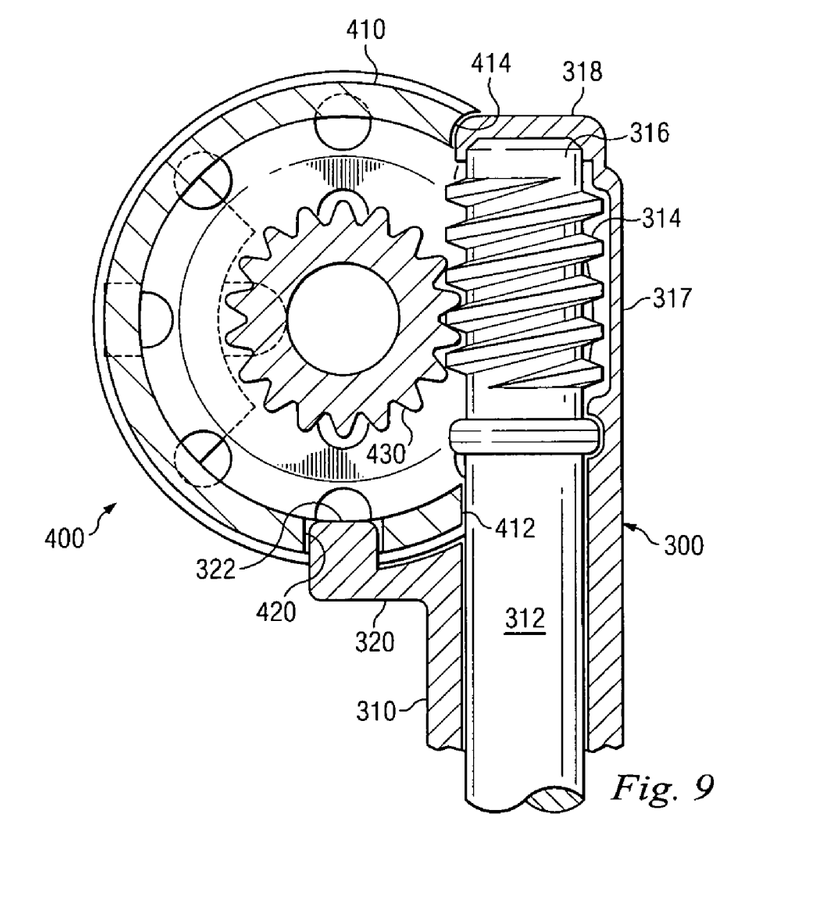
FIG. 9 is a partial longitudinal cross-sectional view of a further embodiment.

Although the above described embodiment has illustrated the worm gear as an integral part of the housing, it is contemplated that the worm gear may be an extension of an internal driveshaft of an insertion tool. Referring now to FIG. 9, an insertion/expansion tool 300 is shown in combination with an expandable implant 400. Expandable implant 400 is constructed virtually identical to implant 100 except protrusion 130 has been replaced with a side opening defined by walls 412 and 414 extending through housing 410. Instrument 300 includes a cannula 310 and an internal drive shaft 312 rotatably disposed therein. Cannula 310 includes a medial projection 320 including a locking projection 322. Drive shaft 312 has a worm gear 314 adjacent its distal end 316. The worm gear is disposed within a protective housing 317 of the cannula terminating in a housing engagement end 318. Thus, the rotating worm gear is shielded from soft tissue surrounding implant 400. It will be appreciated that the worm gear may be positioned adjacent sprocket 430 and caused to rotate such that the sprocket will rotate about the longitudinal axis of the insertion tool. Further, the tool is engaged to the expansion implant 400 on the lateral aspect of the implant such that the instrument does not block the central area of the implantation site. This provides greater visualization of the soft tissues and vertebrae for the surgeon. Once the desired height of the expandable implant 400 has been obtained, the instrument with its associated worm gear may be withdrawn from engagement with sprocket 430 and withdrawn from the patient.

It will be appreciated with respect to FIG. 1, that the entire expansion assembly 200 is contained within housing 110. Thus, all moving components of expansion assembly 200 are shielded from engagement with the surrounding tissues of the body. It will be appreciated that the shielding of the expansion assembly 200 within housing 110 thereby protects the surrounding tissues from potential damage by engagement with any of the expansion assembly components. As will be appreciated, this can be particularly important with respect to significant neural structures such as the spinal cord, dura, exiting nerve roots and adjacent lateral nerves. Further, significant vascular structures extend along the spine including the aorta and vena cava which respond poorly to engagement with abrasive structures due to the pulsatile nature of blood circulation. The unitary outer structure of housing 110 provides a continuous curved surface from atraumatic engagement with surrounding tissue.

Once expandable implant 100 has been expanded to the desired height, a lock screw 128 may be advanced into engagement with upper sprocket 210 and in particular with one of the grooves 218 to prevent further rotation of the sprocket. Additionally, although not required, a further locking screw 129 may be advanced into engagement with lower sprocket assembly 270 and one of the grooves 272. It will be appreciated that locking the relative rotation will insure that the height established during the surgical procedure will be maintained throughout the life of the device. While a pair of locking set screws has been shown for the purposes of illustration, it will be appreciated that other mechanisms and techniques may be utilized to inhibit the relative rotation and encourage maintenance of the established height. For example, it is contemplated that bone growth promoting material such as allograft, autograft, or bone matrix materials may be inserted into the interior 112 of the device after implantation. For example, opening 113 provides access to the interior sufficient to fill the interior. Additional bone growth promoting substances may be inserted through the plurality of apertures 111 extending through outer housing 110. In addition to cooperating to inhibit rotation of the internal components, the bone growth promoting substance may participate in and encourage bone fusion through the interior 112 of the device and between the upper and lower vertebral bodies such as $V_2$ and $V_4$.

While the present device has been described with respect to insertion between two vertebrae after removal of the intervening vertebrae and intervertebral disc, it is contemplated that the length of the device may be sized appropriate to span multiple vertebrae. Additionally, the device may find application in other orthopedic areas and the size and shape of the device may be made to substantially match the implantation site. For example, while the present embodiment has been illustrated as a substantially cylindrical device, it is contemplated that in certain spinal applications it is desirable that the device have a substantially D shaped cross-section as viewed from top to bottom such that the anterior portion of the device has an exterior convexly curved surface matching the anterior of the vertebral body while the posterior portion of the device is substantially flat or concave allowing it to be positioned closer to the spinal canal without protruding into the spinal canal.

Embodiments of the implant in whole or in part may be constructed of biocompatible materials of various types. Examples of implant materials include, but are not limited to, non-reinforced polymers, carbon-reinforced polymer composites, PEEK and PEEK composites, shape-memory alloys, titanium, titanium alloys, cobalt chrome alloys, stainless steel, ceramics and combinations thereof. If the trial instrument or implant is made from radiolucent material, radiographic markers can be located on the trial instrument or implant to provide the ability to monitor and determine radiographically or fluoroscopically the location of the body in the spinal disc space. In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. In some embodiments, a cavity is cut or constructed through the implant. The cavity may be useful to contain grafting materials. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. In other embodiments, the implant may be solid, porous, spongy, perforated, drilled, and/or open.

In some circumstances, it is advantageous to pack all or a portion of the interior and/or periphery of the implant with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor $\beta 1$, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack all or a portion of an unexpanded implant, as shown in FIG. 2, with material and then place the device in the body. Upon expanding the device to an expanded state such as is shown in FIG. 5, material placed in the bone engaging components will be urged against the bone. Additional material may be placed through the outer housing 110 to fill any voids created during the expansion process. Placement of additional material may be accomplished directly or with the aid of an injection or transfer device of any effective type.

Access to the surgical site may be through any surgical approach that will allow adequate visualization and/or manipulation of the skeletal structures. Example surgical approaches to the spine include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated. It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure.

FIG. 1 illustrates four vertebrae, $V_1$-$V_4$, of a typical lumbar spine and three spinal discs, $D_1$-$D_3$. While embodiments of the invention may be applied to the lumbar spinal region, embodiments may also be applied to the cervical or thoracic spine or between other skeletal structures. Further, the end pieces may be angled to achieve or maintain angulation of lordosis or kyphosis between the remaining vertebral end plates. For example, each end plate may have 0°, 3°, or 6° of angulation allowing the device to achieve between 0° and 12° of angulation between remaining vertebrae.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable medical implant for supporting skeletal structures comprising:

a body;
a sprocket disposed within the body having gears configured to receive a turning mechanism to rotate the sprocket, the sprocket including a first end with a threaded portion and a second end with a threaded portion, wherein the gears and the first and second ends of the sprocket are an integral unitary body;
a first end component sized to engage with the threaded portion of the sprocket first end; and
a second end component sized to engage with the threaded portion of the sprocket second end,
wherein the threaded portion of the first end includes right-hand threads, and the threaded portion of the second end includes left-hand threads.

2. The expandable medical implant of claim 1 wherein the body is generally cylindrical.

3. The expandable medical implant of claim 1 wherein the body includes a plurality of openings through which osteogenic material may be inserted and bone growth may occur.

4. The expandable medical implant of claim 1 wherein the sprocket is disposed completely within the perimeter of the body.

5. The expandable medical implant of claim 1 wherein the threaded portion of the first end of the sprocket includes threads on an inside, generally cylindrical surface.

6. The expandable medical implant of claim 1 wherein the threaded portion of the second end of the sprocket includes threads on an inside, generally cylindrical surface.

7. The expandable medical implant of claim 1 wherein the first end component includes bone engaging protrusion to assist in securing the implant to the skeletal structures.

8. The expandable medical implant of claim 1 wherein the second end component includes bone engaging protrusion to assist in securing the implant to skeletal structures.

9. The expandable medical implant of claim 1 wherein the first end component includes openings through which bone growth may occur.

10. The expandable medical implant of claim 1 wherein the second end component includes openings through which bone growth may occur.

11. The expandable medical implant of claim 1 further comprising a worm gear connected to the body and sized to engage the gears of the sprocket.

12. The expandable medical implant of claim 11 further comprising a surgical instrument for turning the worm gear.

13. The expandable medical implant of claim 12 wherein the surgical instrument includes a cannula and an inner shaft disposed at least in part within the cannula, the inner shaft configured to couple with the worm gear.

14. The expandable medical implant of claim 13 wherein the cannula is releasably attachable to the body.

15. The expandable medical implant of claim 1 further comprising a surgical instrument configured to turn the sprocket.

16. The expandable medical implant of claim 15 wherein the surgical instrument includes a worm gear near the distal end of the surgical instrument, the worm gear positionable within the body to engage the gears of the sprocket.

17. The expandable medical implant of claim 1 wherein a location for coupling a surgical instrument to the expandable medical implant is offset from the longitudinal center of the implant.

18. The expandable medical implant of claim 1 wherein one or both of the first and second end components are configured to translate without rotating relative to the body as the implant is expanded.

19. The expandable medical implant of claim 18 wherein a projection extends from the body and inhibits rotation of the first end component relative to the body.

20. The expandable medical implant of claim 19 wherein the projection is a guide pin fixed to the body.

21. An expandable medical implant for supporting skeletal structures comprising:
a body having an exterior surface, the body extending along a longitudinal axis;
an expansion means disposed within the body for converting rotational movement into linear expansion of the implant;
a first end component sized to engage with the expansion means and be moved away from the body by operation of the expansion means; and
a second end component sized to engage with the expansion means and he moved away from the body by operation of the expansion means;
wherein the expansion means is disposed within the body for protection of tissue adjacent to the skeletal structures,
wherein a portion of the first and second end components are disposed within the body when the expandable implant is unexpanded,
wherein the first and second end components translate without rotation in opposing directions along the longitudinal axis when the expansion means converts rotational movement into linear expansion of the implant.

22. The expandable medical implant of claim 21 further comprising a surgical instrument releasably connectable to the body and including means for turning the expansion means.

23. The expandable medical implant of claim 22 wherein the surgical instrument includes a cannula and an inner shaft disposed at least in part within the cannula, the inner shaft configured to couple with the expansion means.

24. A method of placing an expandable medical implant within a spinal column comprising:
making an incision adjacent to a vertebral body;
removing at least a portion of the vertebral body;
providing the expandable medical implant comprising:
a body,
an expansion means disposed within the body for converting rotational movement into linear expansion of the implant, the expansion means having a first end with a threaded portion and a second end with a threaded portion,
a first end component sized to engage with the expansion means and be moved away from the body by operation of the expansion means, wherein a portion of the first end component is disposed within the body when the implant is unexpanded, the first end component having plate with a bearing surface configured to interface with bone structure and bear loading applied by the bone structure, and
a second end component sized to engage with the expansion means and be moved away from the body by operation of the expansion means, wherein a portion of the second end component is disposed within the body when the implant is unexpanded, the second end component having a plate with a bearing surface configured to interface with bone structure and bear loading applied by the bone structure,
wherein the first and second end components translate without rotation in opposing directions along a longitudinal axis when the expansion means converts rotational movement into linear expansion of the implant;

providing a surgical instrument comprising a cannula and an inner shaft disposed at least in part within the cannula, the inner shaft configured to couple with the expansion means;

releasably attaching the cannula to the body;

inserting the expandable medical implant at least in part into a volume left open after removal of the portion of the vertebral body;

rotating the inner shaft to activate the expansion means;

detaching the cannula from the body; and removing the surgical instrument through the incision.

25. An expandable medical implant for supporting skeletal structures comprising:

a body having a longitudinal axis;

a sprocket assembly disposed within the body, the sprocket assembly including a sprocket gear, a first end with a threaded portion, and a second end with a threaded portion, the sprocket gear having teeth that project in a radial direction transverse to the longitudinal axis and being disposed entirely within the body, the sprocket assembly being configured to convert rotational movement into linear expansion of the implant;

a driving gear engaged with the sprocket gear in a manner to impart rotational movement to the sprocket assembly, the driving gear being disposed so as to be accessible from an exterior of the housing;

a first end component sized to engage with the threaded portion of the sprocket first end, the first end component having a bearing surface configured to interface with bone structure and bear loading applied by the bone structure, the first end component including a first channel formed therein in a longitudinal direction;

a second end component sized to engage with the threaded portion of the sprocket second end, the second end component having a bearing surface configured to interface with bone structure and bear loading applied by the bone structure, the second end component including a second channel formed therein in a longitudinal direction, a first pin extending from the housing into the first channel in a manner that mechanically obstructs relative rotation between the housing and the first end component;

a second pin extending from the housing into the second channel in a manner that mechanically obstructs rotation between the housing and the second end component;

wherein the threaded portion of the first end includes right-hand threads, and the threaded portion of the second end includes left-hand threads, the threaded portions of the right and left ends being respectively engaged with the first and second ends with threaded portions in a manner that the first and second end components translate without rotation in opposing directions along the longitudinal axis when the expansion means converts rotational movement into linear expansion of the implant.

* * * * *